US005222479A

United States Patent [19]

Brauer et al.

[11] Patent Number: 5,222,479

[45] Date of Patent: Jun. 29, 1993

[54] OXYGEN SELF-RESCUER APPARATUS

[75] Inventors: Lothar Brauer; Klaus-Dieter Dahrendorf; Volker Hunnebeck; Klaus Haertle; Werner Mascher; Udo Mushold; Klaus Pampuch; Ulrich Timm; Bernd Woicke; Stefan Zloczysti, all of Berlin, Fed. Rep. of Germany

[73] Assignee: Auergesellschaft GmbH, Fed. Rep. of Germany

[21] Appl. No.: 717,863

[22] Filed: Jun. 19, 1991

Related U.S. Application Data

[63] Continuation of Ser. No. 427,763, Oct. 26, 1989, abandoned, which is a continuation-in-part of Ser. No. 13,208, Feb. 6, 1987, abandoned, which is a continuation-in-part of Ser. No. 753,687, Jul. 10, 1985, abandoned.

[30] Foreign Application Priority Data

Jul. 20, 1984 [DE] Fed. Rep. of Germany ....... 3426757

[51] Int. Cl.[5] ............ A61M 15/00

[52] U.S. Cl. ............ 128/202.26; 128/205.12; 128/205.17

[58] Field of Search ............ 128/202.26, 205.28, 128/205.12, 205.13, 205.17, 205.22

[56] References Cited

U.S. PATENT DOCUMENTS

| | | | |
|---|---|---|---|
| 4,019,509 | 4/1977 | Li et al. | 128/202.26 |
| 4,409,978 | 10/1983 | Bartos | 128/202.26 |
| 4,515,156 | 5/1985 | Khudosovtsev et al. | 128/202.26 |

FOREIGN PATENT DOCUMENTS 60930 3/1968 Fed. Rep. of Germany .

*Primary Examiner*—Edgar S. Burr
*Assistant Examiner*—Aaron J. Lewis
*Attorney, Agent, or Firm*—Reed Smith Shaw & McClay

[57] ABSTRACT

A self-contained portable personal breathing apparatus that has a casing housing a canister containing an oxygen evolving chemical. The casing is disposed inside a cover which is disposed inside a bag. The cover and the casing form a thermal insulating pocket between them, and with the cover material and the casing material, also made of thermally insulating material, a triple layer of thermal insulation is formed around the canister to protect oxygen produced therein from the heat of reaction of the chemical in the canister. A heat exchanger is situated atop the canister to further cool oxygen before inhalation, and breathing tube extends from the bag to the user for channeling exhaled breath and oxygen.

10 Claims, 6 Drawing Sheets

OXYGEN SELF-RESCUER APPARATUS

CROSS-REFERENCE TO OTHER APPLICATIONS

"This is a continuation of copending application Ser. No. 07/427,763 filed on Oct. 26, 1989, now abandoned, which was a continuation-in-part of Ser. No. 07/013,208 filed on Feb. 6, 1987, now abandoned, which was a continuation-in-part of Ser. No. 06,753,687 filed on Jul. 10, 1985, now abandoned"

FIELD OF THE INVENTION

The present invention pertains to a respirator used as an oxygen self-rescuer and especially to one used as an escape device.

BACKGROUND OF THE INVENTION

Respirators of the type indicated above are housed in stand-by containers which can be closed airtight and are used, for example, by miners who carry them constantly on their bodies. The device is removed from the stand-by container for use in an emergency. It is obvious that, in terms of weight and size, a respirator of this type must be light and small if it is to be carried about continuously by a miner.

In a known respirator of the general type involved here, the respirator bag is located above the chemical cartridge, and the chemical cartridge is placed int he lower part of the housing; the respirator bag with its breathing hose and mouthpiece are located in the housing cover. In this way, a relatively tall housing cover is required, which therefore plays an important role in determining the overall height of the stand-by container, and as a result the respirator, together with its stand-by container must be worn on the body by means of a shoulder strap. Under the extremely harsh conditions which prevail in mines, this method of carrying the device is burdensome to the miner who must carry the device constantly.

In other patents, such as East German Patent 60930 to Schwanike, there is an attempt to reduce the tallness of the housing by placing a cartridge inside a respirator bag. Thermo-insulting material in the form of protective shields is placed between the respirator bag and the side of the cartridge that rests against the bad to protect the oxygen-filled respirator bag from the intense heat produced by the cartridge during operation. The cartridge is connected for gas flow through an exit portion to the respirator bag and to a valve cage at an entrance portion. The respirator bag is also connected to the valve cage at a different location than the cartridge. Besides the bulkiness of this design, two additional problems exist. The front of the cartridge is exposed to impacts, such as bumps, during the user's work which can compromise the integrity of the cartridge. Also, the structure with its insulating protective shields is heavy to carry over extended periods of time.

The present invention is therefore based on the task of creating an especially lightweight, durable and compact design for an oxygen self-rescuer used as an escape device, and to design it to be so lightweight, durable and compact that the device can be housed in a stand-by container to be worn comfortably on the belt of the person carrying the device during the rigors of the mining work day.

SUMMARY OF THE INVENTION

The present invention provides self-contained portable personal breathing apparatus that has a casing housing a canister containing an oxygen evolving chemical. The casing is disposed inside a cover which is disposed inside a bag. The cover and the casing form a thermal insulating pocket between them, and with the cover material and the casing material, also made of thermally insulting material, a triple layer of thermal insulation is formed around the canister to protect oxygen produced therein from the heat of reaction of the chemical in the canister. A heat exchanger is situated atop the canister to further cool oxygen before inhalation, and a breathing tube extends from the bag to the user for channeling exhaled breath and oxygen.

The advantages obtained from the present invention consist especially in that the size of the respirator is reduced, and thus the device can be housed in a small stand-by container which is worn on the belt. In addition, as a result of the complete, double enclosure of the chemical cartridge, namely, by the cover ant he casing, the surface temperature of the respirator is advantageously reduced.

The invention has demonstrated in a surprising manner that it is possible to locate the chemical cartridge inside the respirator bag, although it was to be expected that the heat given off by the chemical cartridge during operation would represent an unacceptable burden on the respirator bag and on the inhalation air located in the respirator bag. It was to be assumed that, as in the past, because of the known thermal load on the respirator bag, this bag would have to be located part form the chemical cartridge representing a source of heat.

Additional advantageous embodiments of the invention are indicated in the disclosure.

DETAILED DESCRIPTION OF THE INVENTION

Figure 1:
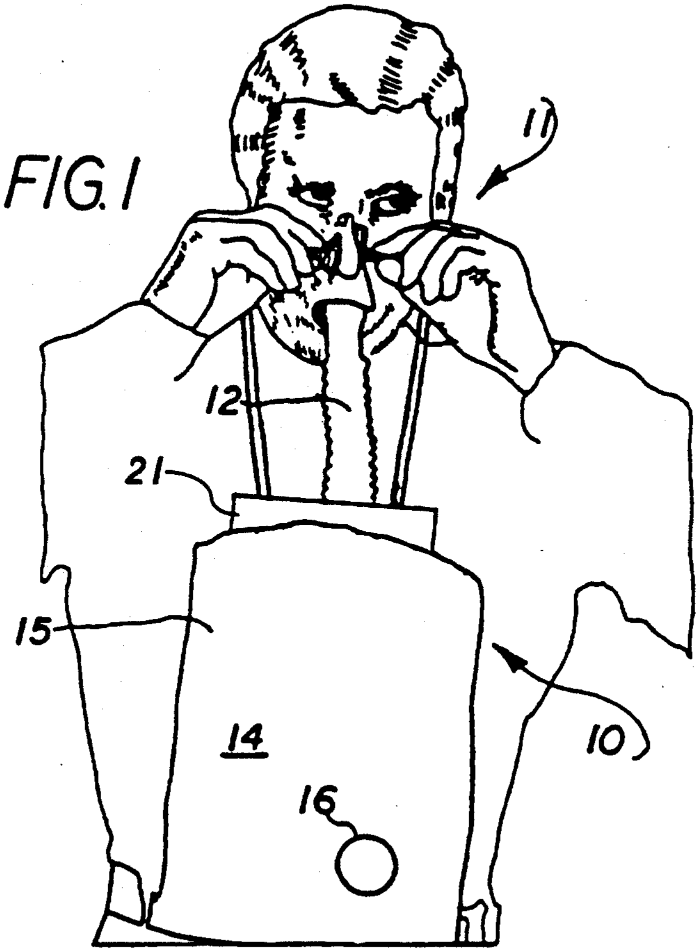
FIG. 1 is a perspective view of the respirator of this invention in working position on a user to be protected.

Referring now to FIG. 1, the apparatus, generally 10, is sen in an operating position, attached about the waist of a user 11. The breathing tube 12 (usually ribbed for durability) extends from the user's mount (being retained by clenching a mouthpiece 17 (See FIGS. 2, 3 and 5–7) behind the teeth or dentures. The tube terminates at the upper surface of an integrated cover 21 for the internal chemical unit which is retained by an adjustable peripheral ring clamp 13. The canister to be described is submerged in the flexible breathing bag 14, which has disposed in its outer surface 15 a one-way, pressure relief value 16. When the gases contained within the bag (mostly oxygen) reach a pressure of about 2.5 millibars, then the valve is gated to release some gas to avoid abnormal stresses on the respiratory tract of the respirator user.

Figure 2:
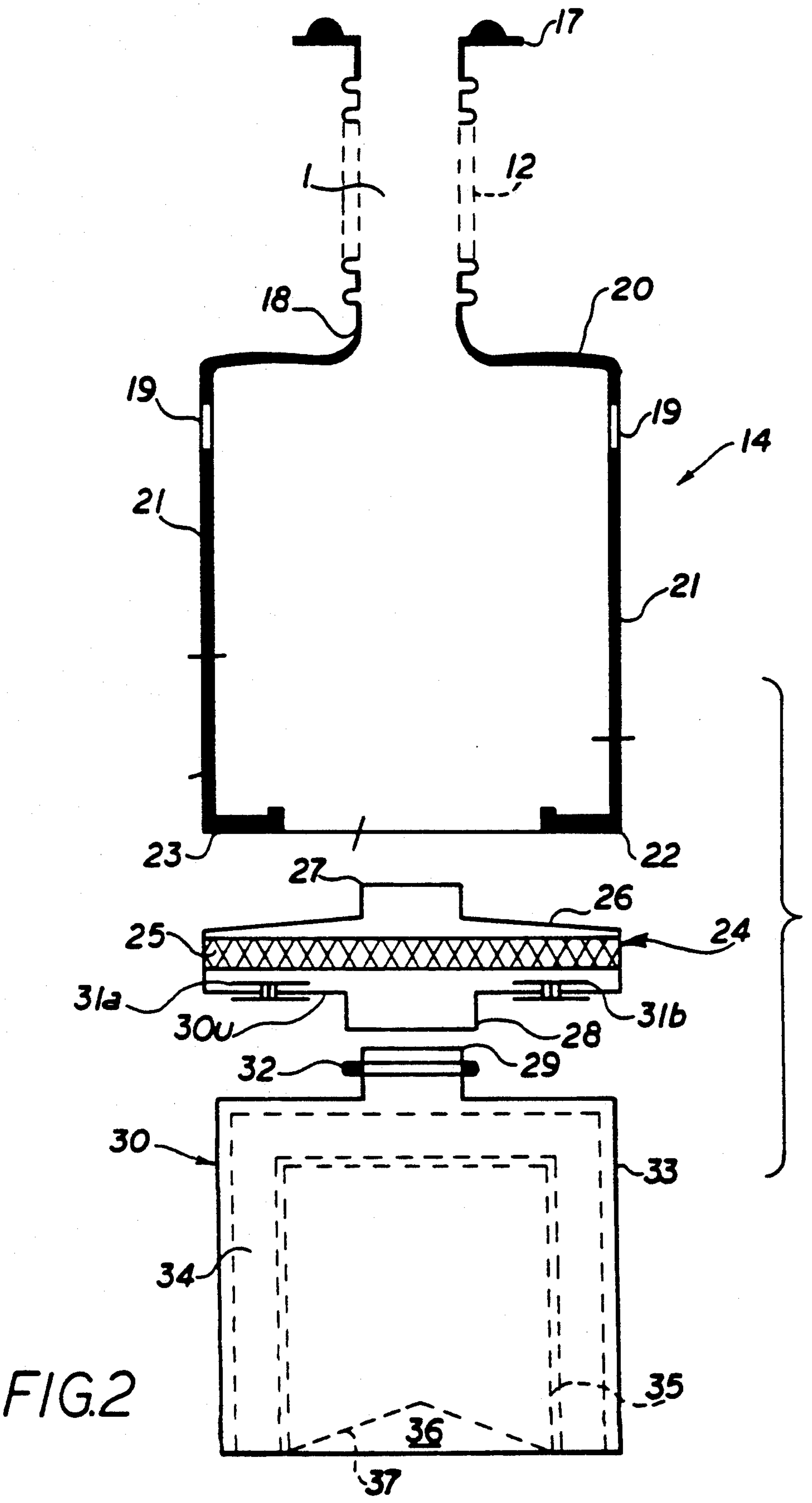
FIG. 2 is a vertical section of an exploded view of the main components of the respirator in a first embodiment.

In the exploded full sectional view of FIG. 2, the mouthpiece 17 operatively connects via breathing tube 12 to an outwardly flanged collar 18 of a flexible elastomeric material cover 21, effecting a hermetic seal. In the same embodiment described assembled in relation to FIG. 5 (the circulating respiration mode), a plurality of slot-like openings 19 are provided on the laterally opposed sides of the cover 21. The lower periphery 22 of flexible cover 21 is turned inwardly and reinforced thus forming flange 23, but still providing a substantial opening to admit other components. Components 12 and 17 are preferably fabricated of silicon polymer systems.

The heat exchanger component, generally 24, is of a disc-shaped configuration, with the heat exchanger itself 25 disposed internally thereof. The upper surface 26 slopes upwardly and encloses a centrally positioned short vertical neck 27 that sealingly engages the inside of collar 18 of the cover, upon assembly. The unit's lower surface has downwardly flanged central collar 28, that will encompass the open central neck 29 of the chemical-bearing canister generally 30. Dispose dint he under-periphery 30*u* of unit 24, are a pair of one way, check valves, 31*a* and 31*b*, which operate to prevent escape of exhaled breath when working in the circulating mode but allow oxygen to flow therethrough during inhalation. A retention ring 32 is disposed about the canister neck 29, which will permit an air-locking fit with the internal surface of collar 28.

Canister 30 has an impervious metal casing 33 which encloses a particulate mass of chemical of the special function described above, and is further provided with a large internal recess, giving the chemical mass 34 the configuration of an inverted urn. A gas permeable liner material 35 retains the formed shape of particulate chemical so that it may function as will alter be described. The lowest area of recess portion 36 has a concave screening element 37 which will retain drippings form the liquefying chemical.

Figure 3:
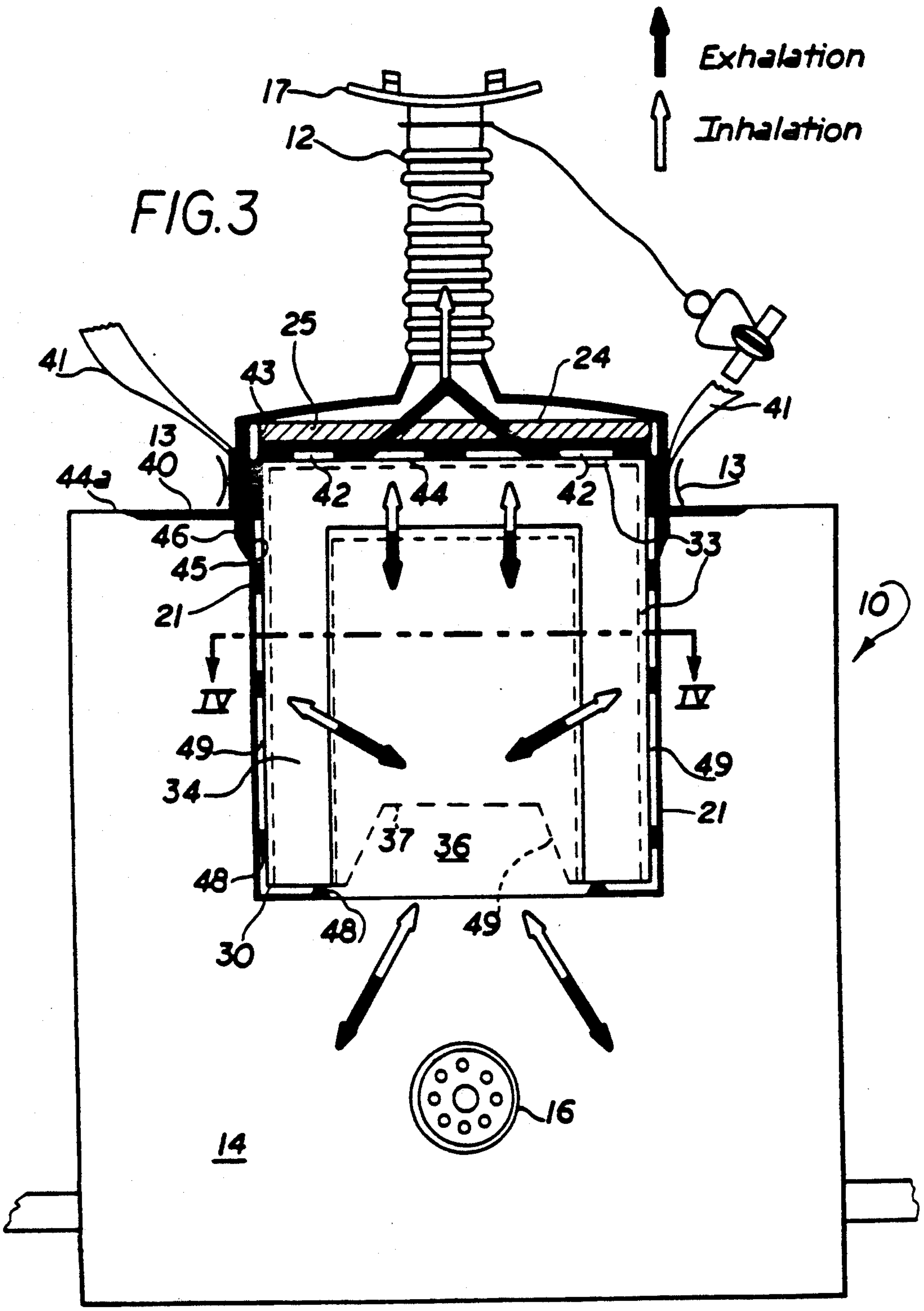
FIG. 3 is a vertical schematic diagram of the another respirator embodiment in vertical section while in the alternating (pendulum) mode of operation.

FIG. 3 shows an alternative embodiment of a breathing apparatus according to the present invention rigged with pendulum mode of respiration. The respirator consists of an oxygen-evolving chemical cartridge 34 which is tightly surrounded by a thermally insualting and impact-absorbing casing 33, a breathing tube 12 with a mouthpiece 17, a cover 21 enclosing the chemical cartridge 34 and a carrying strap 41. One established oxygen emittive (generating) chemical is potassium superoxide ($KO_2$), which is most usefully employed herein in a particulate form that has a stable particle size even when subjected to shaking and variations in ambient temperature. The utility of $KO_2$ stems from its chemical, thermic and mechanical properties, including $O_2$ generation on user demand and effecting a simultaneous removal of much of the exhaled carbon dioxide ($CO_2$) thus avoiding the need for an absorbent material in the pack. The exhaled $CO_2$ serves to react with the potassium superoxide forming potassium carbonate and thus generating oxygen along with that oxygen being produced by the moisture in the exhaled breath.

The mouthpiece 17 ant eh breathing tube 12 are preferably composed of the same material as the casing 33, namely from a silicon rubber. The cover 21 to be described is made of a rubberized life jacket type fabric, such as of polyamide fiber.

Above the gas inlet opening(s) 42 of the chemical cartridge 34, there is the heat exchanger component 24, which is designed in such a way that no thermal contact can occur between the heat exchanger 25 and the chemical cartridge 34. The heat exchanger 25 is peripherally surrounded by a thermally insulating housing receptacle 43, which rests on the upper surface 44 of casing 33 above the chemical cartridge 34 in such a way that it cannot be dislodged.

The reduction of the surface temperature of the chemical canister is vitally important for the reaction that during the breathing with the apparatus, transient short-duration temperatures as high as +250° C. can be reached. It goes without saying that such temperatures must be reduced in order that the user of the apparatus does not burn himself. The "heat exchanger" 25 has the function of cooling the inhaled air before it enters into the breathing tube. It removes the heat during the inhalation and passes it to the air exhaled in the next step. The inhaled air after cooling through the heat exchanger has a temperature of about 70° C.

On the upper end surface 44*a* of the respirator bag 14, a large opening 45 is provided, through which the chemical cartridge 34 and casing 33 is inserted into the respirator bag. Opening 45 bordered by a vertical peripheral flange 46 on cover 21 to which the chemical cartridge 34 with its casing 33, and the ends of the carry strap 41 are sealingly secured by means of a clamping ring 13. A pressure-relief valve 16 is provided on the front surface 15 of the breathing bag 14.

The lower end surface of the chemical cartridge 34 is only partially enclosed by the covering 21 so that the underside outlet opening 36 of the chemical cartridge is freely accessible to the flow of air being inhaled and exhaled (FIG. 3). The upper end surface of the cartridge 34 is completely covered by the covering 21, which preferably forms a unit with the breathing tube 12 (FIG. 3).

Figure 4:
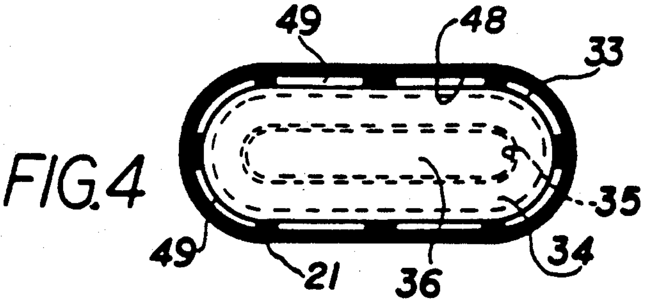
FIG. 4 is a transverse sectional view of the embodiment of FIG. 3 as seen along lines IV—IV.

In FIG. 4, is shown a horizontal cross section taken through the chemical cartridge 34 along line IV—IV of FIG. 3, with its cover 21. The cover 21 has number of inward ribs 48 which are located at spaced intervals from each other and rest firmly against the casing 33, in either the vertical or longitudinal axis.

The cover 21 consist of a thermally insulating material, such as of silicon elastomers. This cover 21 helps to minimize the thermal stress during use of the respirator bag 14 surrounding the chemical cartridge 34, resulting rom the exothermic reaction occurring upon activation of the oxygen evolving chemical. Because the cover 21 is designed with internal ribs 48, resting firmly against the lateral surface of casing 33 which surrounds the chemical cartridge 34, intermediate spaces 49 are formed around the periphery between the outer wall of the casing 33 and the cover 21. These spaces 49 act as a thermal insulation zone and reduce the surface temperature of the cover 21. This is the key to the invention. By utilizing the internal ribs 48 to create a thermal insulation zone, essentially three layers of insulation are provided between the chemical cartridge 34, wherein intense heat is present because of the chemical reaction to process the exhaled air, and the space within the bag 14 where the oxygen produced form the chemical reaction resides By surround the canister 30 with three layers of insulating, the three layers being the cover 21, the spaces 49 and the casing 33 (each limiting the remnant of heat transfer), the oxygen in bag 14 is maintained at a cooler level than otherwise possible with a chemical canister in the bag. The heat exchanger 25 is then able to provide oxygen to the user at a temperature comfortable for breathing.

The triple layer insulation structure provides the unexpected and beneficial result that the chemical filled canister 30 can be located inside and totally surrounded by the bag 14, thus saving space during operation. This is important in a mining situation and especially important in the situation when the apparatus is required to be used where it si extremely undesirable to have a bulky breathing apparatus getting in the way while escape is being attempted. The structure of cover 21 with ribs 48 also lead t further advantages. It is easier to draw the cover 21 over the canister 30 containing the chemical cartridge 34 during assembly.

The weight of the cover 21 is reduced, so that the weight of the unit to be worn on the belt becomes less. This is important because a user commonly wars the breathing apparatus throughout the day. The lighter the weight of the apparatus, the less tiring it is for the user and the more efficient he is at his job. Furthermore, the stiffness of the cover 21 is increased. Overall, cover 21 also serves as an impact absorber for the respirator housed in the stand-by container (not shown). This is important because the canister 30 holding the chemical cartridge 34 may possibly receive constant bumping as teh user carries out his daily functins. If the cartridge 34 is comprised from an impact, the apparatus 10 does not operate effectively. The cover 21 not only acts as an insulation layer, but also s a first layer of impact absorption, with the insulation space 49 providing leeway for the cover 21 to bend under an impact without tearing and without the canister 30 receiving a blow, or a reduced in energy blow if the cover 21 is depressed enough by the impact.

In order to obtain optimum use of the oxygen-producing chemical, and thus a longer period of use from the respirator for the person carrying it, it is necessary to try to obtain uniform flow conditions across the entire volume of the chemical mass. This is achieved by means of the largest possible flow contact surface, in that the exhaled air of the person wearing the device flows through the breathing hose 12 into and through the chemical cartridge 34, axially from the bottom in the upper region, and radially from the outside toward the inside in the lateral area. The air outlet surface projects domelike into the chemical cartridge 34. The flow through the cartridge is indicated by the arrows seen in FIG. 3.

Also, in order to prevent dust form the chemical from reaching the breathing bag 14 from the cartridge, the air outlet surface 35 is advantageously loosely surrounded by a cotton wadding (not seen) which holds back the dust. In order to prevent molten chemical from possibly running out of the canister 30 in the breathing bag 14, the air outlet opening 36 of the cartridge has a surface covered by a concave screen 37, projecting upwardly into the opening. This screen can thus divert molten chemical into a collecting pan provided underneath in the chemical cartridge without blocking the flow route.

Figure 5:
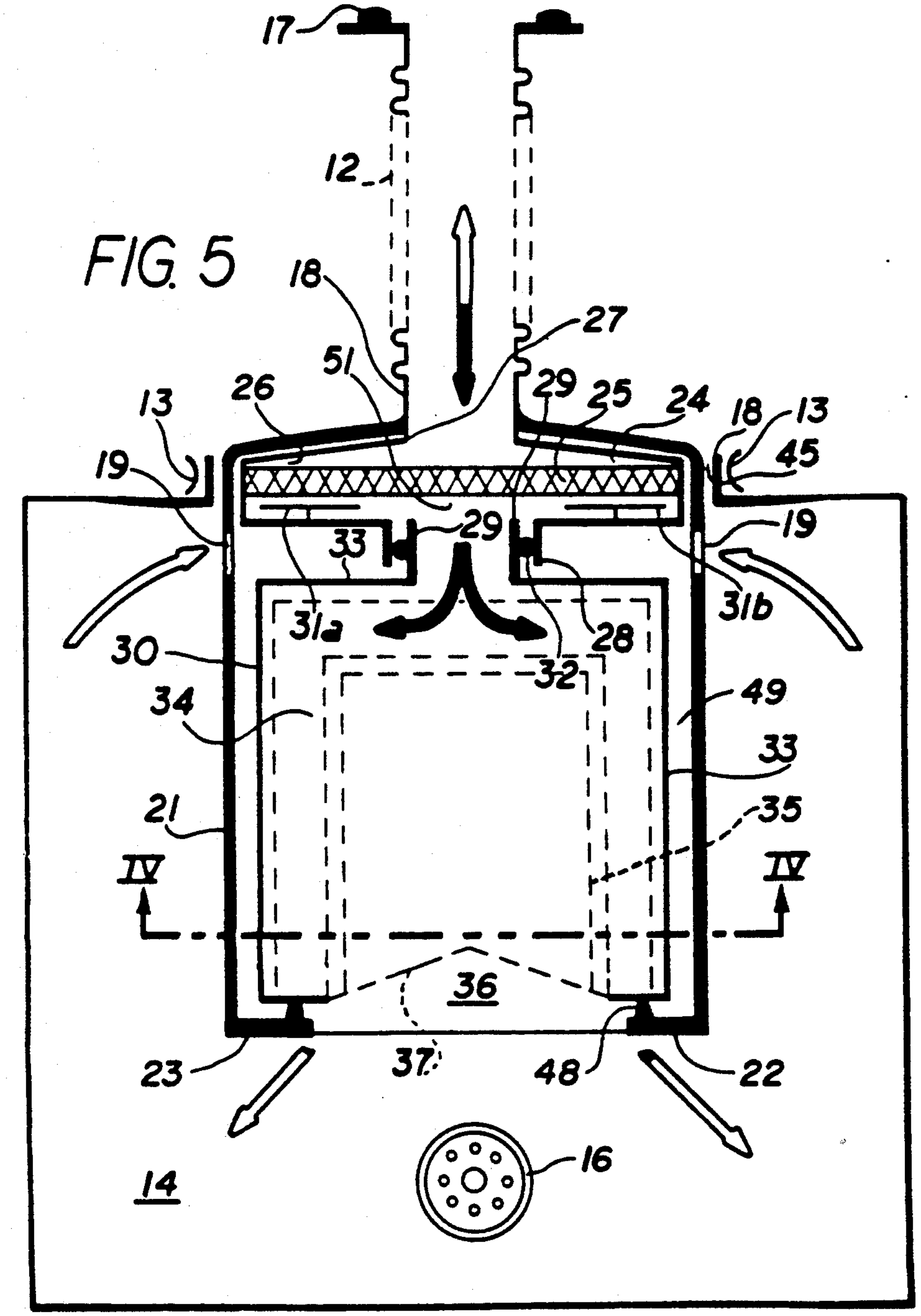
FIG. 5 is a schematic diagram of the first embodiment of the invention while int he circulating mode of respiration.

FIG. 5 shows the operating mode for the breathing bag of the present invention for a circulating respiration. The structure is essentially identical to that shown in FIG. 3, except for the two, one way exhalation check valves, 31*a* and 31*b*, adjacent the heat exchanger element 25. The heat exchanger housing 24 can be plugged into the inlet opening 29 of the chemical cartridge 34 by means of a connector collar 28, projecting downwardly over the inlet opening 29. connector collars 28 and 29 are sealed off by means of a ring gasket 32. Bag opening 45 is sealed by peripheral clamp 13. This heat exchanger chemical cartridge structure is then surrounded by cover 21, as shown in FIG. 2 and described above, and inserted through the inlet opening 45 of the breathing bag 14. A clamping ring 13 wraps around flange 18 of bag surface 15 fixedly clamping bag 14 to the top of cover 21. The cover forms an insulation pocket 40 around the canister of the purpose described above. This embodiment down onto utilize ribs to achieve the pocket 49 but instead relies on the canister 30 being suspended from heat exchanger component 24 to remaining place in cover 21. At least two ribs are located on the bottom of cover 21 at opposite sides of recess 36, that serve as an exit port, of the canister to rest upon (the same is applicable of the embodiment shown in FIGS. 6 and 7, except the canister is positioned and suspended via clamp 13 rather than by entry port 29 and exit port 28).

In the circulating mode of operation (FIG. 5), tube 12 is used exclusively for inhalation ad expiration, and the low of gasses as indicated by the arrows occurs. Upon inhalation, oxygen store din bag 14 is drawn therefrom via cover breathing ports 19 through one-way valves 31*a* and 31*b*, through exchanger component 24 and breathing tube 12 into the user's mouthpiece 17. Upon exhalation, breath containing $CO_2$ passes back down tube 12, but, because valves 31*a* and 31*b* are closed to that flow direction, it si directed through canister collar 29 into the canister 30 and passes through the chemical mass 34 and permeates finally into canister recess 36, thereby generating oxygen by the aforedescribed chemical reaction. The $O_2$ flows from the recess 36 to within breathing bag 14, until drawn upon during the next inhalation cycle. The flow through the chemical mass 34 is indicated by the dual-headed arrows in this schematic, that is, from recess 34, into bag 14.

Thusly, the embodiment of FIGS. 2 and 5 is capable of functional oxygen generation when the tube 12 is used exclusively for inhalation and expiration. The embodiment of FIG. 3, on the other hand, severs only in alternating mode of respiration so that breath passes back and forth through the canister chemical mass, absorbing $C_2$ in one leg, and generating $O_2$ in the other leg, then passing back to the user.

Figure 6:
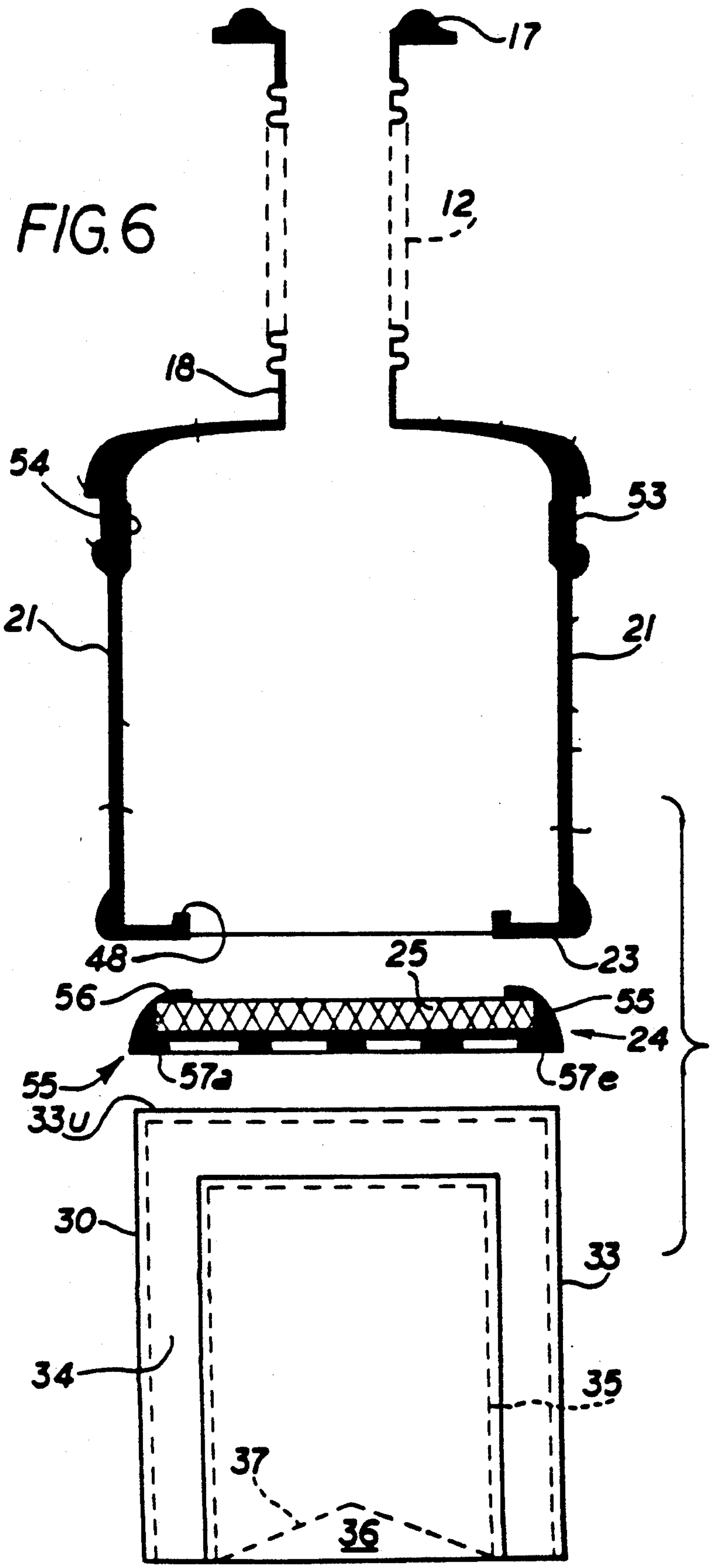
FIG. 6 is a vertical section of an exploded view of the main components of the self-rescuer in a third embodiment for pendulum breathing.

In FIG. 6 is seen an exploded view, in full vertical section, of another embodiment of the present invention, especially adapted for the pendulum mode of breathing, in which like parts will be referred to by like reference numerals. The mouthpiece 17 operatively connects via breathing tube 12 to an upwardly flanged central collar 18 in the upper surface of elastomeric cover 21. This cover is essentially identical in overall configuration with cover 21 of the embodiment shown in FIG. 3, but it down omit the internally projecting ribs 48 of the earlier described embodiment. Note the peripheral recess 53 in the upper portion of flexible cover 21, which receives a clamping ring (not shown) that will hermetically seal the cover inner surface 54 against the peripheries of the heat exchanger component 24 and of inverted canister 30 containing a chemical cartridge 34. Lower flange 23 on cover 21 is highly flexible and thus serves to admit by force-fitting the heat exchanger component 24 and canister 30.

Exchanger component 24 is somewhat differently configured form that of the earlier described embodiment. The heat exchanger 25 is retained peripherally and supportively by an integrated elastomeric frame, generally 55. A peripheral lip 56 on upper frame 55 embraces the periphery of the exchanger element 25. The underside of frame 55 is provided with a plurality of downwardly projecting ribs 57*a* through 57*e*, which serve to space apart the exchanger element 25 from the upper casing surface 33 of canister 30. The configuration of canister 30 is almost identical to the embodiment of FIG. 2, lacking only the centrally located open collar 29 of that embodiment, which serves to form a sealed communication passage with mating collar 28 of heat exchanger assembly 24. In this embodiment, upon assembly, canister 30 abuts ribs 57*a* through 57*e* of the exchanger 25, being spaced apart therefrom only by these ribs.

Figure 7:
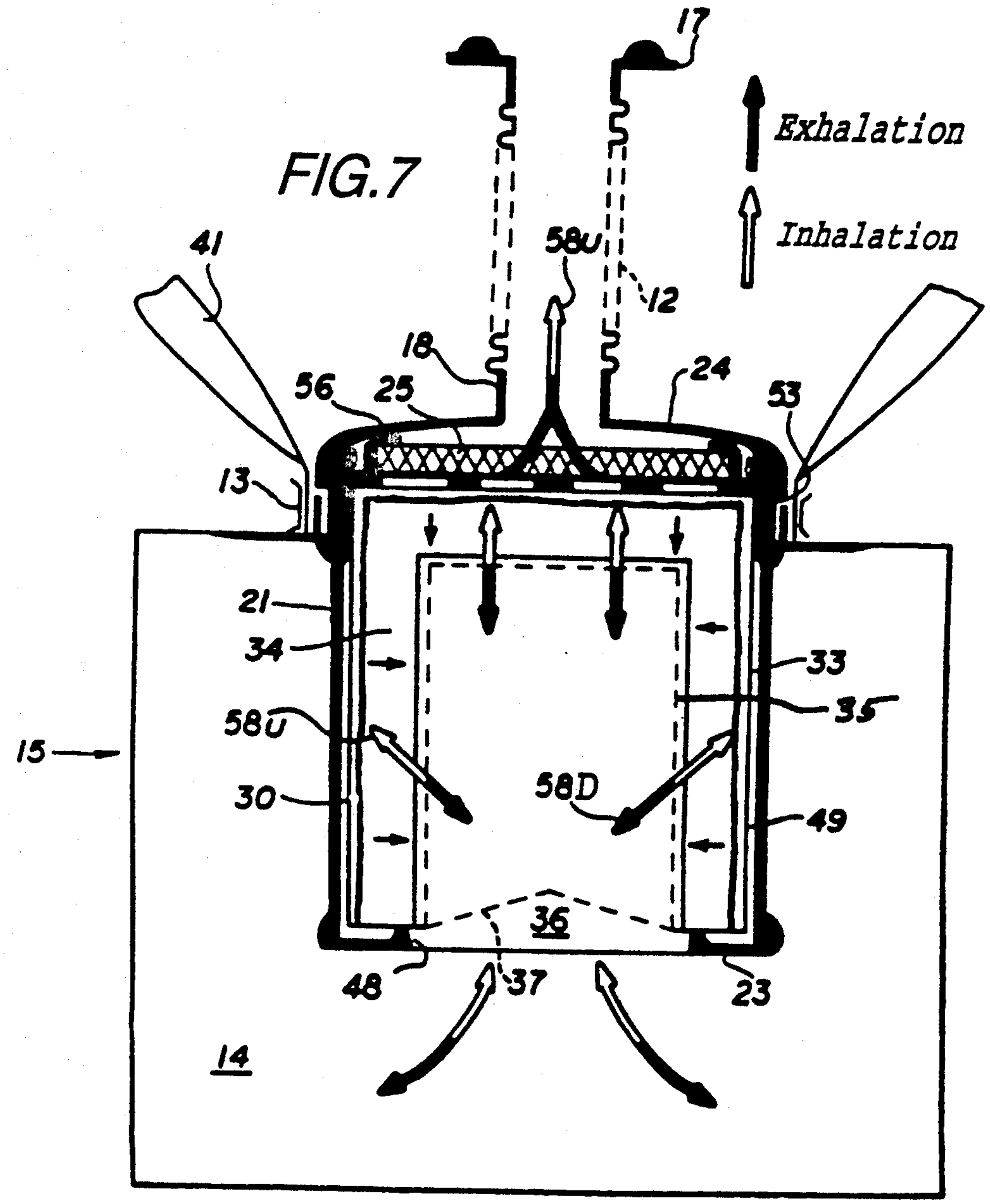
FIG. 7 is a schematic diagram of the third embodiment of FIG. 6 assembled while in the pendulum mode of operation.

In FIG. 7 is shown the operating mode for the embodiment of FIG. 6 int eh pendulum mode of respiration. Bag 14 lacks the check valve 16 of the embodiment of FIG. 3. The whiteheaded arrow ends, like 58, show the direction of gas flow upon inhalation, while the blackheaded arrow ends 58D show the gas flow direction upon exhalation.

GENERAL INSTRUCTIONS FOR PERSONAL RESPIRATOR USE (First Embodiment of FIGS. 2 and 5)

The collapsed respirator is drawn from a standard rigid protector casing and arranged on the chest of the user. The neck and waist straps are adjustable and serve to anchor the apparatus to the operating position. After the mouthpiece 17 is donned, the breathing bag 14 is inflated by exhaling through he tube several times. The nose clip is then fitted and depending upon the specific embodiment being employed, the device can be operated in either mode described above.

When the oxygen source in the canister is spent, the chemical containing canister is readily replaced. A screw driver will loosen retaining clip 13 sufficiently to separate the spent canister from its cover 21 by lifting both from within bag 14.

Next, cover 21 is peeled off the canister 30, the heat exchanger unit 24 is split from the canister and the latter is trashed. A fresh canister is combined with the apparatus parts in the reverse order. Finally, resort to a screw driver serves to resecure the covered canister within the breathing bag.

While a presently preferred embodiment of practicing the invention has been shown and described with particularity n connection with the accompanying drawings, the invention may be otherwise embodied within the scope of the following claims.

What is claimed is:

1. In a self-contained, personal breathing apparatus adapted for pendulum breathing including a canister, a supply of an oxygen-evolving chemical filling the canister and adapted to react with carbon dioxide and water vapor in exhaled breath to generate oxygen, a flexible breathing bag having an input port and an output port and operationally connected to an access opening int eh canister, a mouthpiece connected to a breathing tube which in turn is operationally connected to a second access opening of said canister, and a carrying strap to permit portability of the apparatus, the improvement comprising:

(a) the chemical-filled canister is suspended through the input port substantially within and surrounded by the breathing bag and is spaced apart from the breathing tube;

(b) said canister is covered on the majority of its external surface by a casing adapted to serve as a thermal insulating layer;

(c) a cover surrounds the casing on the majority of its external surface and is spaced part therefrom to form an intermediate space therebetween; and (d) a generally disc-shaped heat exchanger component for cooling inhaled air, the heat exchanger component being situated within the cover and interposed between the breathing tube and the canister to prevent thermal contact of the tube and the canister an to permit both inhaled and exhaled air flow therebetween.

2. The apparatus of claim 1 in which said cover comprises an elastomeric silicon polymer system.

3. The apparatus of claim 1 in which said cover is provided with a plurality of longitudinal ribs on the inside surface thereof in contact with the casing which serve to define the intermediate space comprising a plurality of insulation pockets.

4. The apparatus of claim 1 in which said cover extend over an upper surface but not over a lower surface of said canister and casing so that open communication of gas flow between the bag and the canister is maintained.

5. The apparatus of claim 1 in which the input port of the breathing bag is sized to receive and retain during use the canister, its casing and the cover.

6. The apparatus of claim 5 in whcih the input port is provided with a flange element abutting an upper edge of the cover which flange has a clamping band adapted to cause sealing closure of the bag to said upper edge.

7. The apparatus of claim 1 in which the cover is provide with an outwardly projecting peripheral bead at each end of its vertical sides which serve as shock absorbers between the canister and the opposing walls of the support container.

8. The apparatus of claim 1 in whcih a heat exchanger is interposed between the breathing tube and an upper surface of said canister and being spaced apart to prevent thermal contact with the latter and is secured on its periphery by a retaining element which rests on the upper surface.

9. The apparatus of claim 8 in whcih the retaining elemetn comprises a material with low thermal conductivity.

10. In a self-contained, personal breathing apparatus adapted for closed-circuit breathing including a casing containing a canister, a supply of an oxygen-evolving chemical filing the canister and adapted to react with the carbon dioxide and water vapor in exhaled breath to general oxygen, a flexible breathing bag having an input port and an output port and operationally connected to an access opening of the canister, a mouthpiece connected to a breathing tube which in turn is operationally connected to a second access opening of said canister and a carrying strap to permit portability of the apparatus, in which:

(a) the chemical-loaded canister is suspended substantially within the breathing bag and is spaced apart from the breathing bag;

(b) said canister is covered on the majority of its external surface by a conformed covering sleeve adapted to serve as a thermal insulating layer, which is operatively connected to the breathing tube;

(c) a formed mass of oxygen-emittive chemical is disposed within and its outer surface is in close proximity but spaced apart from the internal surface of said canister;

(d) an enlarged recess defined by the inner surface of said formed mass which provides for flowing communication between the chemical surface and the interior of the breathing bag.

(e) a generally disc-shaped heat exchanger component for cooling inhaled air, the heat exchanger component being situated within the covering sleeve and interposed between the breathing tube and the canister to prevent thermal contact of the tube and the canister and to permit both inhaled and exhaled air flow therebetween;

(f) at least one opening in the lateral wall of said covering sleeve positioned adjacent to he space between the upper surface of the canister and the lower surface of the heat exchanger component; and (g) a gated valve means disposed in said lower surface of said heat exchanger component and adapted to permit oxygen gas contained in said breathing bag to flow from the latter through said component into said breathing tube upon user inhalation, and also adapted to prevent expelled breath from said user form entering said breathing bag without first passing through said formed mass to generate oxygen.

* * * * *